United States Patent
Lakusiewicz

[11] Patent Number: 6,030,354
[45] Date of Patent: Feb. 29, 2000

[54] ENHANCED SLING DEVICE

[76] Inventor: Ronald J. Lakusiewicz, 1316 Euel Rd., Poplar Bluff, Mo. 63901

[21] Appl. No.: 08/960,917

[22] Filed: Oct. 30, 1997

[51] Int. Cl.[7] .............................. A61F 5/00; A61F 13/00
[52] U.S. Cl. ................................. 602/4; 602/60
[58] Field of Search .............................. 602/4, 5, 19, 20, 602/61, 62; 128/869, 874, 875, DIG. 19; 2/44, 45

[56] References Cited

U.S. PATENT DOCUMENTS

| | | | |
|---|---|---|---|
| 4,550,724 | 11/1985 | Berrehail .................................. | 128/874 |
| 4,716,895 | 1/1988 | Marques et al. ............................ | 602/4 |
| 4,733,658 | 3/1988 | Ruthven, Jr. ................................ | 602/4 |
| 4,788,972 | 12/1988 | DeBusk ...................................... | 602/5 |
| 5,129,406 | 7/1992 | Magnusen et al. ...................... | 128/873 |
| 5,598,583 | 2/1997 | Victor et al. ............................ | 602/19 X |
| 5,628,725 | 5/1997 | Ostergard ................................ | 602/61 X |

*Primary Examiner*—Richard J. Apley
*Assistant Examiner*—Denise Pothier
*Attorney, Agent, or Firm*—Blackwell Sanders Peper Martin

[57] ABSTRACT

An enhanced sling device is adapted to be worn on the torso, upper extremities, and shoulders of a wearer to thereby support, immobilize, and elevate either the right or left injured upper extremity or full shoulder of the wearer. The device features a panel of flexible material of one piece construction with smoothly contoured perimeter. The panel is flat, with a front surface and a back surface, but flexible enough to contour to the convex and concave surfaces of the upper extremities, shoulders, chest and back of the wearer. The flexible panel has a one piece "T" configuration with a horizontal segment and a vertical segment which is shorter in overall length than the length of the horizontal segment. The horizontal segment and the vertical segment are foldable to envelop the upper extremity on which the device is worn suspended from the shoulders, chest and back of the wearer; and a plurality of individual pieces of hook and loop fastener material are placed on the front surface of the panel, substantially adjacent to the ends of each of the horizontal segment and the vertical segment to provide fixation of the panel of flexible material at preselected points, to thereby provide a sling device which is multifunctional and adapted for use on either the right or left extremity.

18 Claims, 8 Drawing Sheets

ENHANCED SLING DEVICE

BACKGROUND OF THE INVENTION

1. Field of the Invention

This invention relate to the field of orthotic devices, and particularly to an orthotic device adapted to be worn on an upper extremity suspended from the shoulders and upper back and capable of being immobilized to the torso to protect an injured upper extremity during the interval phase of injury healing.

The invention is a one piece foam device hat is pre-cut of a specific size and shape that attains support for upper extremity injuries using placement of hook and eye attachment material of the type known by the trademark VELI-CRO that adhere directly to the foam being sewn into a fixed position. The invention is multifunctional acting as an extremity elevator when a person is reclining, a sling support against gravity when a person is vertical and upright; and a total upper extremity immobilizer holding a person's upper extremity firmly and gently against the chest with a person in any position and actively mobile. The invention uses no straps or buckles of any kind and permits "on the fly" (very quick) modifications of its shape and integrity without any loss of functionality in order to adapt to the state of the art external fixators and both rigid and soft upper extremity immobilization dressings such as casts. The construction of the invention is of two alternative modes. The first is totally of open-cell foam; the second is of a fabric lamination on one side of the foam. The invention is of universal design being equally applicable for right or left upper extremity support and is designed to accommodate virtually any upper extremity injury.

2. Description of the Related Art

Upper extremity injuries of all kinds such as fractures, dislocations, burns, tendon, nerve and arterial injuries have been and will continue to be problems that will be with us forever and demand ancillary support to whatever mode of treatment that has been selected. These injuries all have special needs that must be satisfied and these needs are the reasons for the multitude of upper extremity support devices available today. A specific type of immobilizer, sling, or elevator exists for each type of condition creating too many individual solutions, none of which address all the problems of all upper extremity injuries. In addition to the discomfort of the injury to the upper extremity itself, many of the existing upper extremity support devices are themselves uncomfortable to wear because of abrading binding straps that twist; cumbersome buckles; and the nature of the support devices to ride out of position. Sleeping in a support with these drawbacks is very difficult and therefore, patient compliance to constantly wear the support (which is important) is greatly reduced thus compromising care and healing. After years of cumulative experience of many surgeons, the necessity of having one, simple, cost effective, upper extremity support device that is capable of addressing all problems of all upper extremity injuries regardless of their treatment modality became obvious.

The present invention is designed to solve all the above problems and to be made easily available to any person with an upper extremity injury either by direct purchase through a public retail store, or applied at a hospital or by emergency personnel in the case of more severe injury.

BRIEF SUMMARY OF THE INVENTION

The present invention is an upper extremity support device that is of one piece construction, made of open cell foam, that has a specific pre-cut shape ready to use "out of the box". Although produced in three size configurations, small-medium-large, the present invention was designed to accept "on the fly" modifications with scissors without destroying the integrity of the invention; and to accept "on the fly" modifications with scissors to allow protrusion of such devices as state of the art external bone fixators without destroying the functionality of the invention. There are no buckles or straps. The invention is fastened at the key points of suspension-fixation by hook and loop style attachments that adhere directly to the open cell foam. The back of the attachment material is sewn to the foam.

The invention is applied by first placing the device in the hook and loop attachment material side up position. The attachment material is always in a non-contact position relative to the skin. As the invention design is universal either right or left, the forearm is then placed in the central member of the invention, the central member wrapped around the forearm until the attachment material of the central member meets the foam of the horizontal "T" portion of the invention thus creating a complete roll of foam around the forearm with the attachment material facing away from the body. The side member of the suspensory segment is then wrapped around the injured upper extremity between the elbow and shoulder beginning between the chest and the arm, encircling the arm until its hook and loop material attaches directly to the foam at a position of comfort facing away from the body.

The suspensory segment of the invention is then passed up over the shoulder of the injured upper extremity and in doing so automatically creates a pocket into which the elbow of the injured upper extremity is supported. The suspensory segment of the invention is then passed behind the neck and down along the front of the chest on the uninjured side. The attachment material at the end of the suspensory segment is then mated to the foam on the side member of the immobilization segment with the side member mating via the hook and loop fastener material with the foam of the suspensory segment. The elbow is now firmly secured in a pocket and the injured upper extremity is now fully suspended and supported.

If only suspension is required, then the invention is modified with scissors by cutting off the immobilization segment just beyond its side member which is attached to the suspensory segment. However, if full shoulder and upper extremity immobilization and extremity elevation is required, the immobilization segment is left intact and then passed around the lower back, to attach by its attachment material end to the foam of the side member of the suspensory segment at the point where the side member already is attached to the suspensory segment. Thus, a support pocket is created for the hand of the injured upper extremity, and the injured upper extremity is firmly but gently secured against the chest.

If elevation of the injured limb is necessary, the immobilization segment is then released from its hook and loop attachment to the side member of the suspensory segment thus allowing elevation to an I.V. pole by attaching the immobilization segment to the suspensory segment which has been released from the side member of the immobilization segment. This creates a double fastener material to foam attachment producing a loop of foam that can be suspended from an I.V. pole.

The advantages of the present invention are:
1. Can be used for any injury of the upper extremity.
2. Addresses all aspects of care for upper extremity injuries of immobilization, suspension and elevation.

3. Can be easily applied either by the injured person solely, or by hospital personnel in an operating room or emergency room setting or by emergency medical technicians at the scene of an accident.
4. Is universal with right and left upper extremities supported by the same sling.
5. Comes in three sizes of small, medium, large to allow immediate use.
6. Permits "on the fly" adjustments with scissors without destroying integrity of invention.
7. Permits "on the fly" adjustments with scissors to accommodate protruding external bone fixators without destroying functionality of invention.
8. Eliminates need for multiple models and styles of immobilizers, slings, and elevators and therefore, allows much more efficient use of inventory space.
9. Is simple in design and production concept.
10. Is compressible for efficient use of space.
11. Washable with soap and water.
12. Eliminates pressure and abrasion caused by casts pressing against the body. As the cast is completely encased in foam.
13. Eliminates problem of cloth slings riding-up on cast immobilizers.
14. Extremely comfortable to wear because there is no abrasion or cutting in from twisting straps or buckles.
15. Very comfortable to sleep in.
16. Can be worn either external to clothing or comfortably in direct body contact.
17. Open cell foam allows air circulation and fluid drainage.
18. Better patient compliance for use because of advantages 12. 13, 14, 15, 16 and 17.
20. Accommodates bare arms and dressings of all kinds including plaster and fiberglass casts; and external bone fixators.
21. Non-allergenic.
22. Instant, easy removal in case of emergencies.
23. Completely x-ray penetrable for evaluation of upper extremity fractures and associated chest injuries.

DETAILED DESCRIPTION OF THE INVENTION

Figure 1:
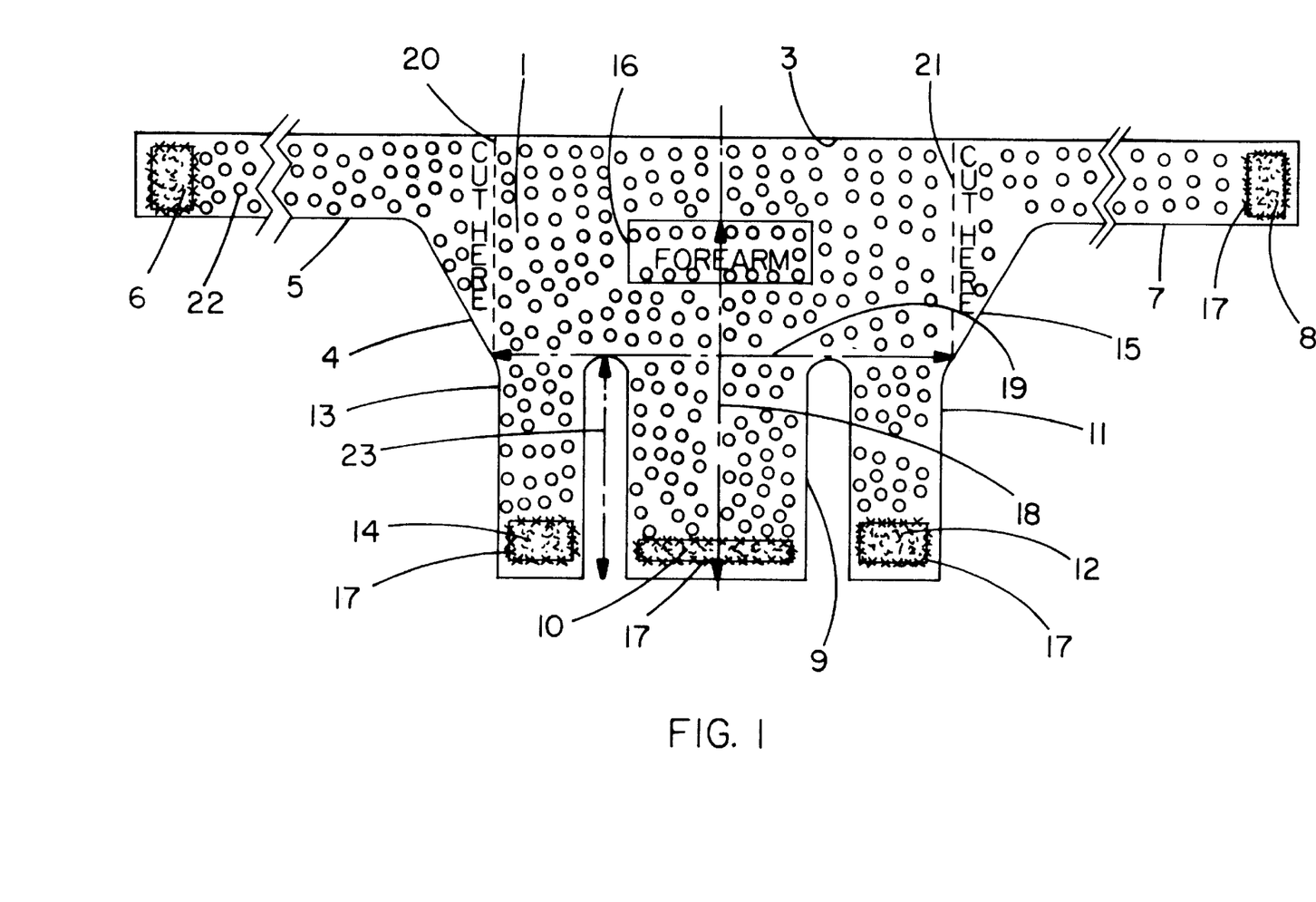
FIG. 1 is a front perspective view of the invention showing its "T" shape configuration and showing that all hook and loop style fasteners are located on the front side. Also is shown the imprinted label stating the word "Forearm" and also the imprinted designation with dashed line labeled "Cut Here" at the junction of the immobilization member and suspension member with the vertical member.
Figure 2:
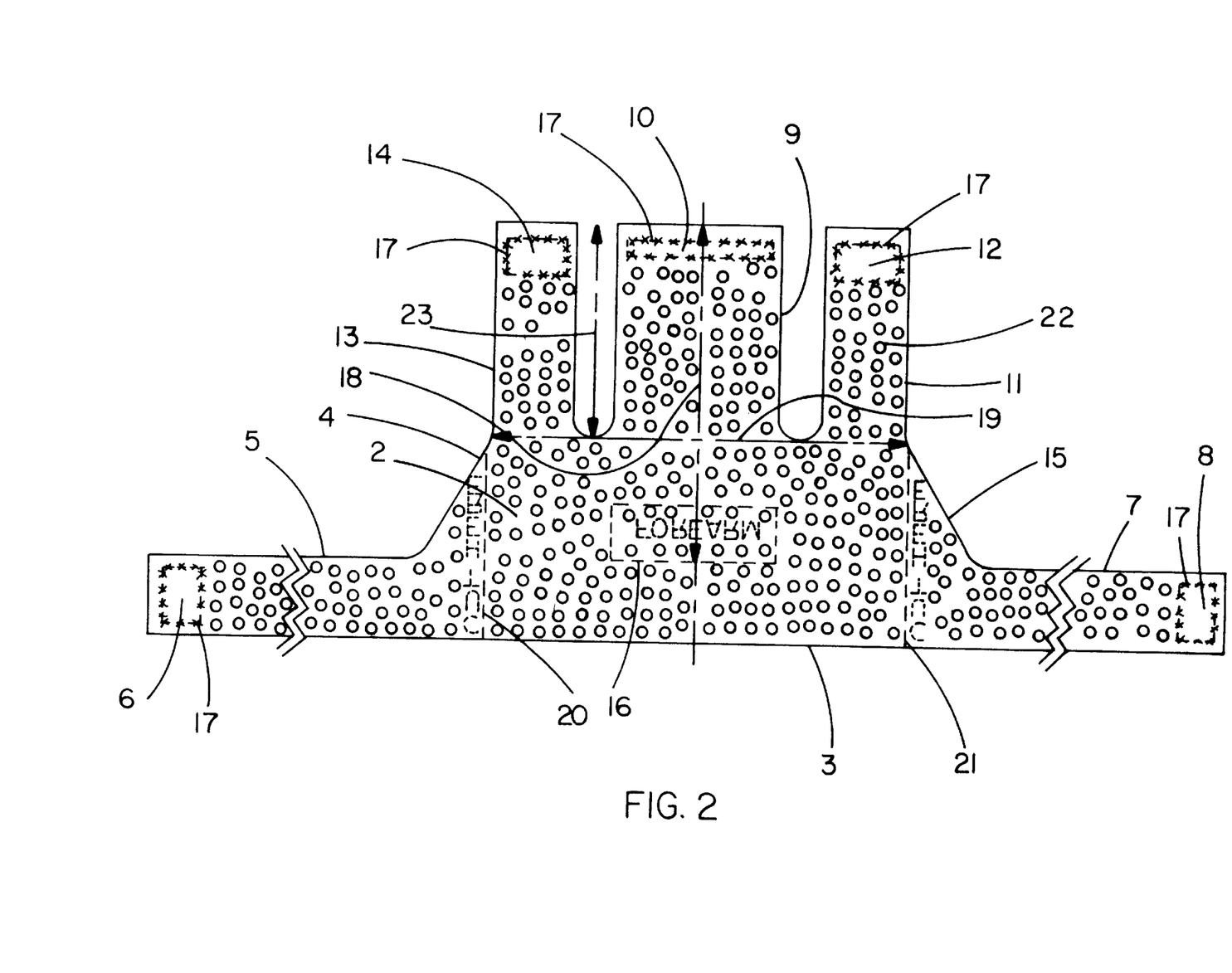
FIG. 2 is a rear perspective view of the invention showing that there are no hook and loop style fasteners located on the rear side.

An unassembled frontal view of the invention which is constructed according to the principles of this invention is shown in FIG. 1; as is an unassembled rear view of the present invention shown in FIG. 2.

Figure 3:
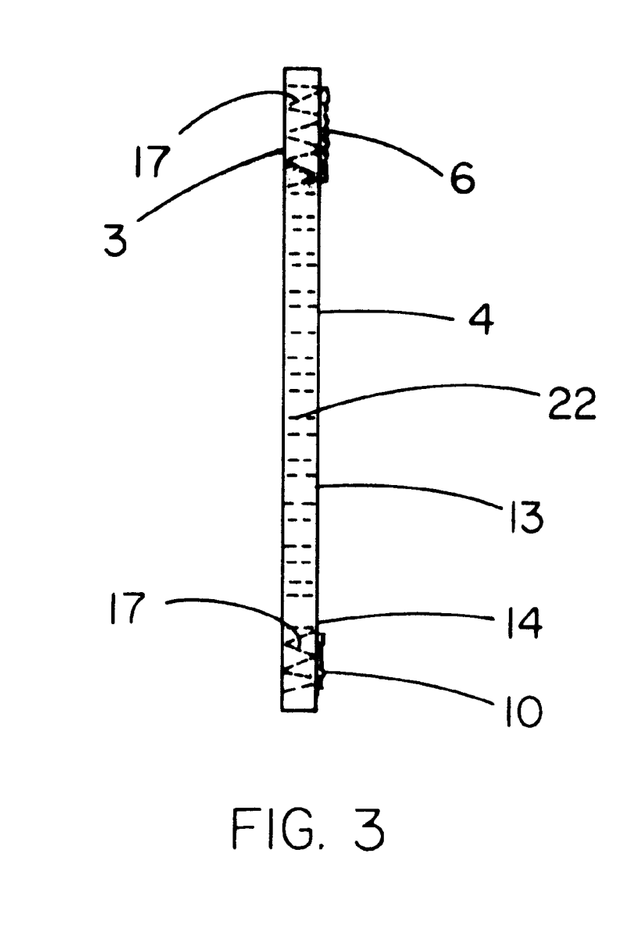
FIG. 3 is a side perspective view of the invention showing the immobilization end.
Figure 4:
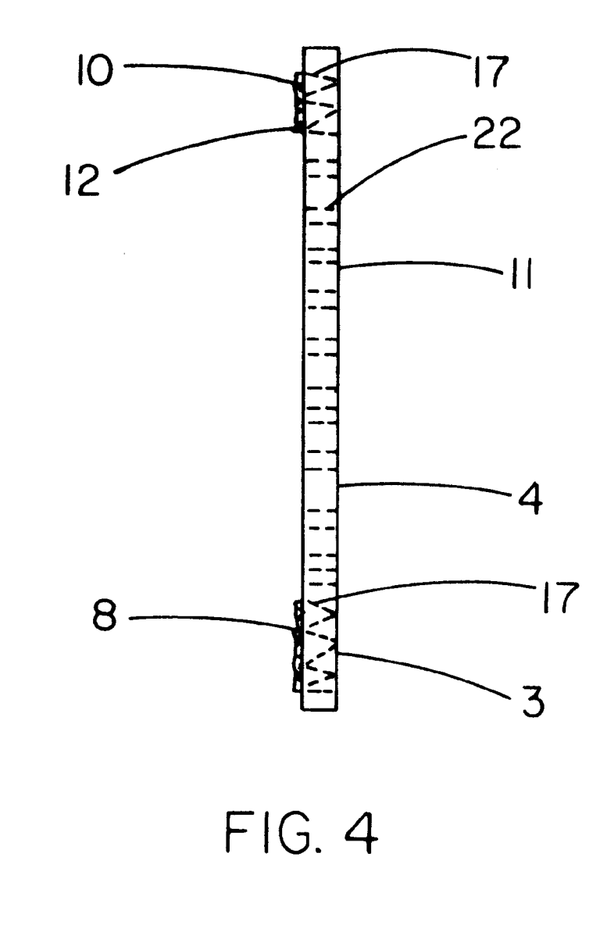
FIG. 4 is a side perspective view of the invention showing the suspension end.

Similarly, an unassembled side view of the invention is shown in FIG. 3 depicting the immobilization side of the invention; and an unassembled side view of the invention is shown in FIG. 4 depicting the suspension side of the invention.

Figure 5:
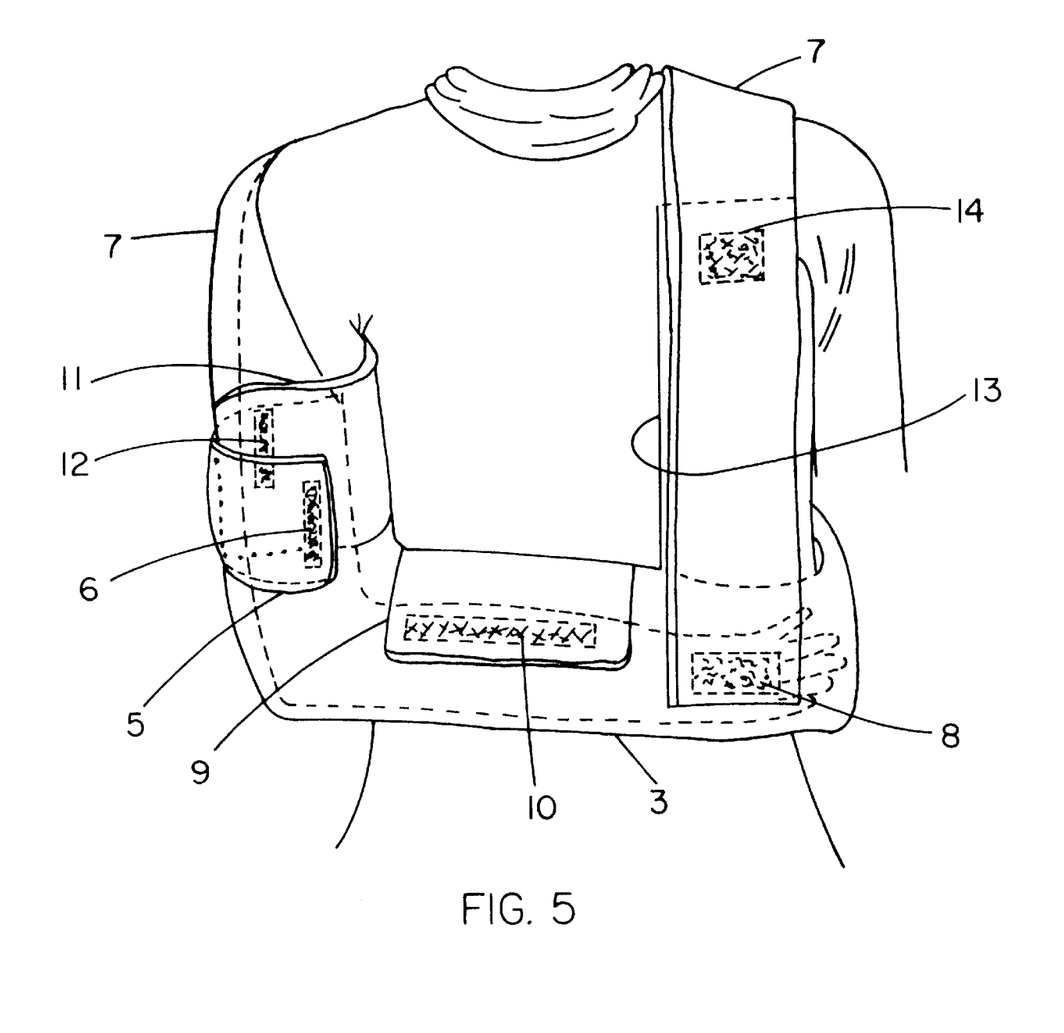
FIG. 5 is a front perspective view of the torso of a person wearing the invention fully assembled in the immobilization mode.

A fully assembled invention in the immobilization mode is shown in frontal view in FIG. 5 as it would be worn on the torso of a person to fully support and hold the upper extremity firmly to the chest to prevent motion of the upper extremity away from the body. FIGS. 5–9 are drawn without perforations, for clarity.

Figure 6:
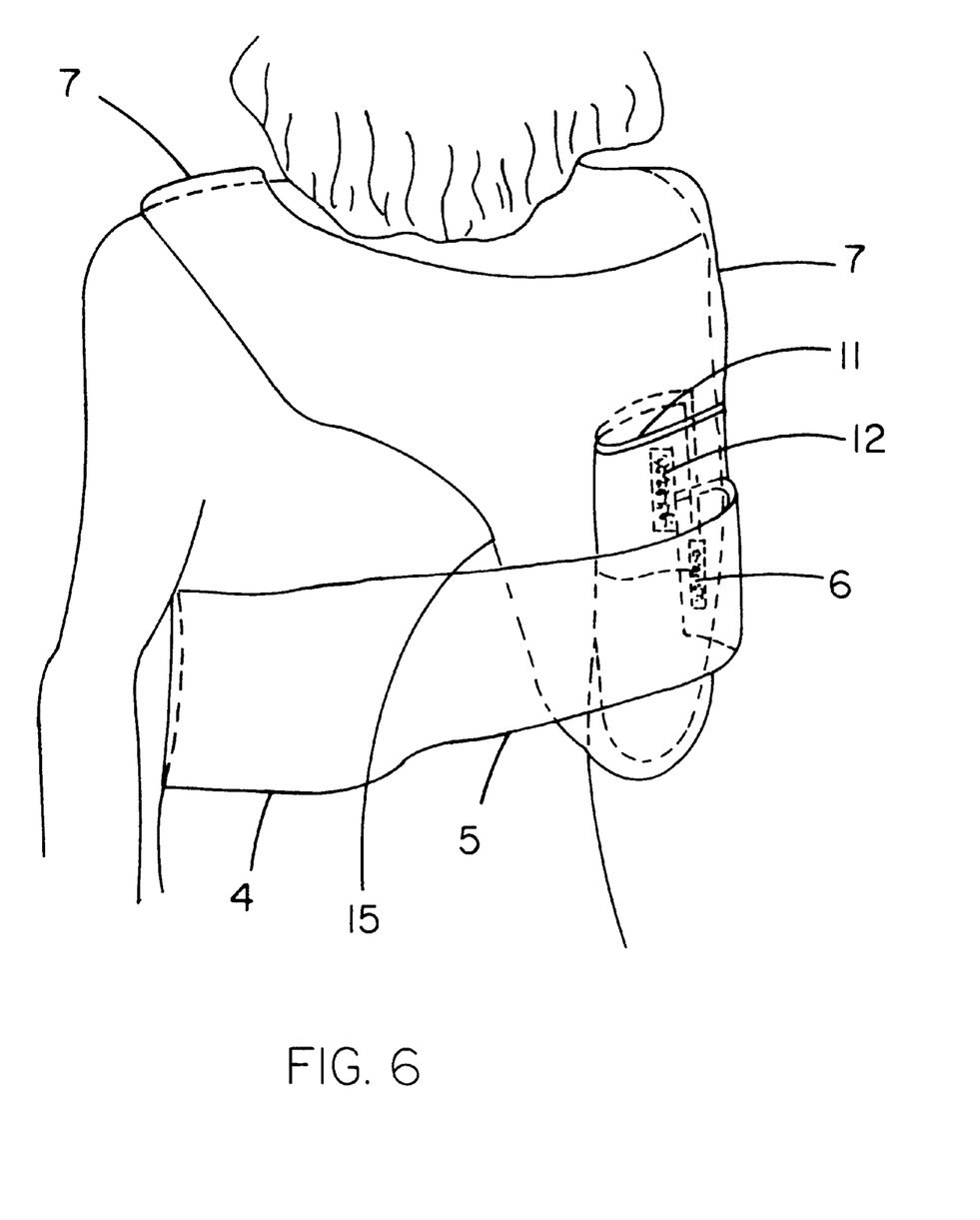
FIG. 6 is a rear perspective view of the torso of a person wearing the invention fully assembled in the immobilization mode.

Similarly, a fully assembled invention in the immobilization mode is shown in rear view in FIG. 6 both supporting and holding the upper extremity firmly to the chest.

Figure 7:
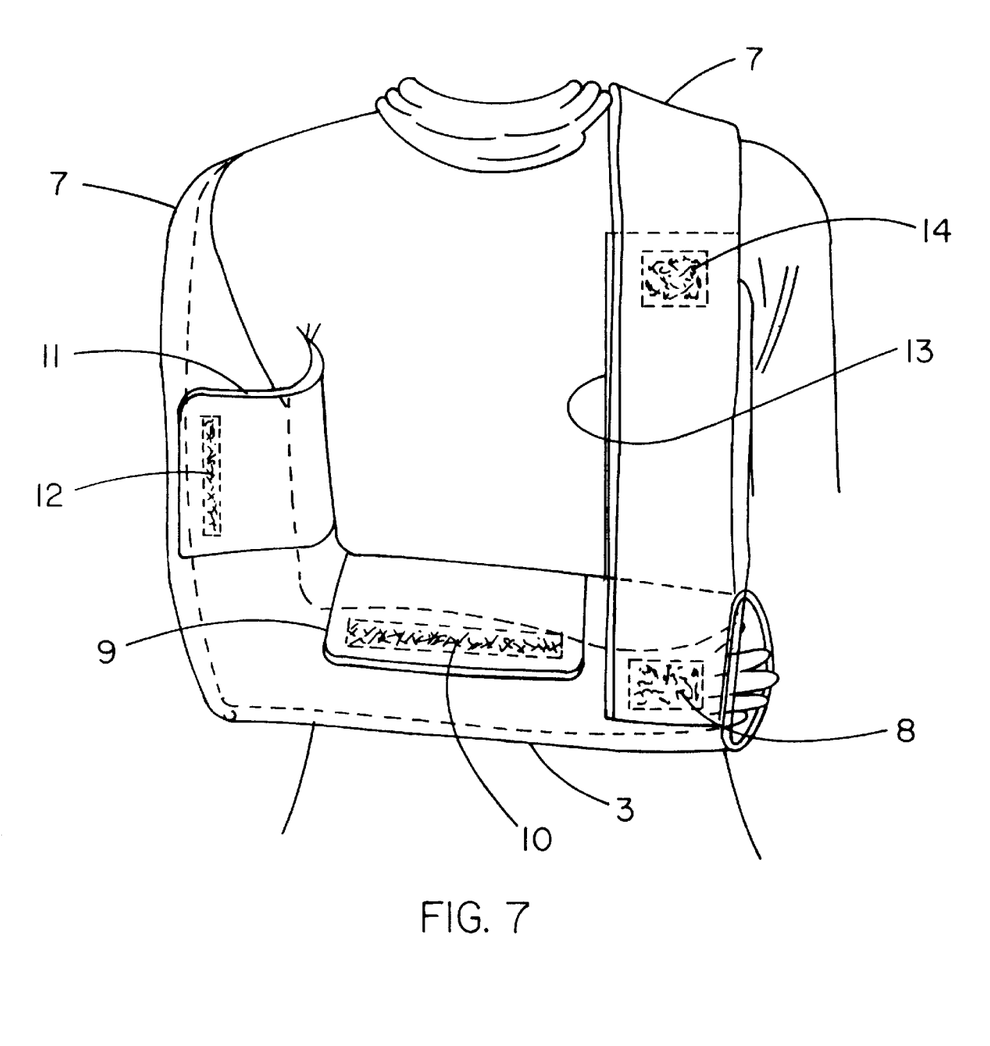
FIG. 7 is a front perspective view of the torso of a person wearing the invention partially assembled in the suspension mode with the immobilization segment removed.
Figure 8:
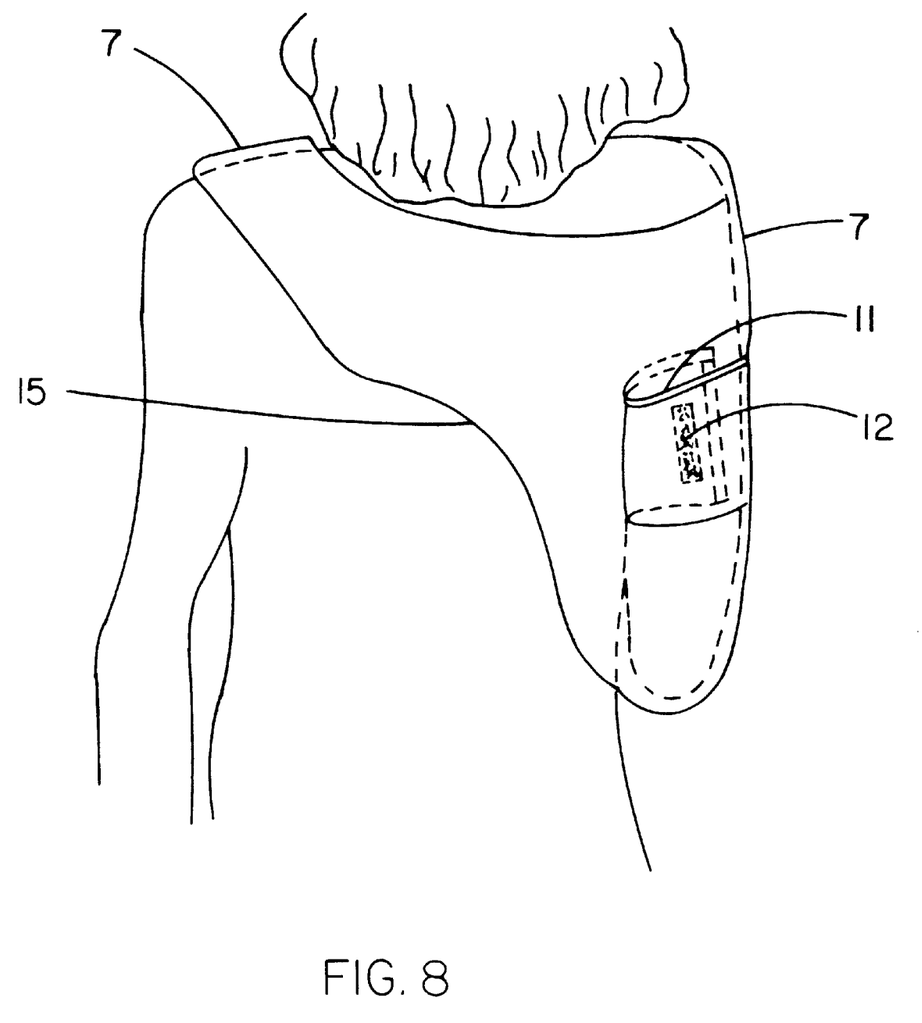
FIG. 8 is a rear perspective view of the torso of a person wearing the invention partially assembled in the suspension mode with the immobilization segment removed.

A fully assembled invention in suspension mode only, which supports the upper extremity against gravity, but does not prevent motion of the upper extremity away from the chest is shown in frontal view in FIG. 7 and in rear view in FIG. 8, as the invention would be worn by a person.

Figure 9:
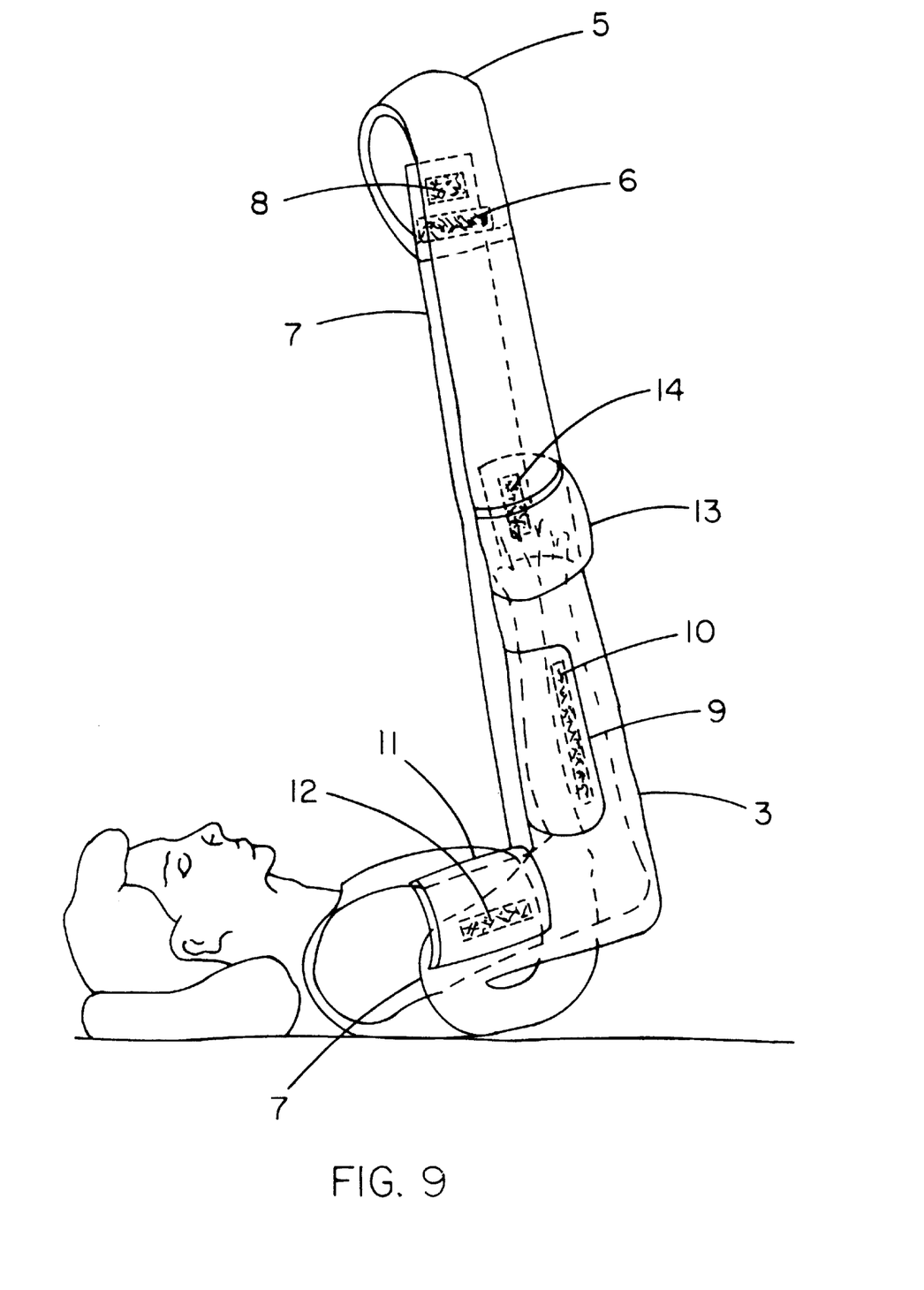
FIG. 9 is a lateral perspective view of the torso of a person in the reclining position wearing the invention in the fully assembled configuration suspended to some abstract structure for the purpose of elevating the upper extremity. Corresponding reference numerals indicate corresponding parts throughout the several views of the drawing.

A fully assembled invention in elevation mode is shown in FIG. 9 as it would be worn by a person for maintaining the upper extremity higher than the heart to decrease swelling when the person is reclining.

The invention is of universal design for application to a right or left upper extremity requiring the upper extremity to be placed into the invention with the forearm resting at the junction of the central member 9 and the "T" segment 3 in the label imprinted on the front face FIG. 1 of the invention marked "Forearm" 16. For a right upper extremity, the hand automatically faces in the direction of the immobilization segment 5 and the elbow faces in the direction of the suspensory segment 7. For a left upper extremity the hand automatically faces in the direction of the suspensory segment 7 (which for a left upper extremity becomes the immobilization segment functionally) and the elbow faces in the direction of the immobilization segment 5 (which for a left upper extremity becomes the suspensory segment functionally).

The entire invention is of one piece construction made completely of either polyether open cell foam 1, or a nylon laminated polyether open cell foam product number 050200002 by Catalyst International Company onto the front surface FIG. 1 of which are sewn multiple pieces of hook and loop fastener or attachment material 6, 8, 10, 12, 14 with polyester/cotton button thread 17. The invention has a uniform thickness of 0.25 inch, with multiple perforations 22 preferably of circular configuration that are non-confluent, separated by varying distances, and extending through the entire thickness of the invention opening onto each surface of front and back to dissipate heat, and the overall configuration in the front view FIG. 1 and rear view FIG. 2 is "T" shaped with the longer horizontal segment 3 of the "T" having the same width as the side member 13 of the immobilization segment 5 and the side member 11 of the suspension segment 7. The vertical segment of the "T" is shorter and confluent with the horizontal segment of the "T" having its sides 4, 15 angled at 60° where the vertical and horizontal "T" segments join in order to create a pocket for the hand and elbow. The vertical segment is further composed of three parallel and separate vertical members 9, 11, 13. The central member 9 of the vertical segment is twice as wide as each of side members 11, 13. Each side member 11, 13 is separated from the central member 9 by a distance equal to ½ the width of a side member 11, 13. All junction corners are rounded to decrease point concentration stress forces which is helpful in reducing tendency to tear. The length of the central member 9 and two side members 11, 13 is equal. All hook and loop fasteners 6, 8, 12, 14 are centrally located one inch in from the end of the front FIG. 1 of each segment 5, 7 and each side member 11, 13 and measure three inches by two inches. The hook and loop fastener material 10 of the central member 9 is also centrally located one inch in from the end of the front FIG. 1 of the central member 9 and measures one inch long by seven inches wide for rapid, efficient, "out of the box" use. the invention is presented in three sizes of small, medium and large.

Measurement for the three size configurations are:

LARGE: Horizontal segment 3 equals eight feet long by four inches wide. Vertical segment length 18 equals eighteen inches. Vertical segment width 19 equals twenty inches. Length 23 of The central member 9 and both side members 11, 13 equals twelve inches.

MEDIUM: Horizontal segment 3 equals eight feet long by four inches wide. Vertical segment length 18 equals sixteen inches. Vertical segment width 19 equals twenty inches. Length 23 of the central member 9 and both side members 11, 13 equals nine inches.

SMALL: horizontal segment 3 equals five feet long by three inches wide. Vertical segment length 18 equals thirteen inches. Vertical segment width 19 equals eight inches. Length 23 of the central member 9 and both side members 11, 13 equals eight inches.

The vertical segment is confluent and centrally located relative to the horizontal segment in all sizes.

OPERATION

The present invention is quickly and easily put on. Because the invention addresses the three functions of immobilization, elevation, and suspension and is applied in a different assembly configuration for each of the aforementioned functions, the application of the invention will be described separately for each function.

If the invention is to be applied solely and completely by the wearer, it is easiest to apply the invention while sitting down in a chair, especially if a hard cast or external bone fixator is already attached to the upper extremity.

I. For Immobilization

Place the invention on the lap of the wearer in its fully open, unassembled configuration with its front view FIG. 1 up, so that all imprinted labels 16, 20, 21 and hook and loop fasteners 6, 8, 10 12. 14 arc visible to the wearer and the vertical segment 18 extended toward the wearer. The forearm of the involved upper extremity is placed on the imprinted label marked "Forearm" 16 such that the long axis or length of the forearm is in line with the length of the "Forearm" label 16. The central member 9 of the vertical segment 18 is then wrapped around the involved forearm and the horizontal segment 3 attaching the central member 9 by its hook and loop fastener 10 to the foam rear surface 2 of the horizontal segment 3. Thus creating an encircling roll around the forearm. The invention is now completely attached to the involved forearm.

The side member 11 of the suspension segment 7 is passed between the chest and the involved arm from posterior to anterior and held in this position by gentle pressure of the involved arm pressing the side member 11 against the chest. With the opposite hand, the suspension segment 7 with its fastener 8 facing the wearer is lifted across the arm of the involved upper extremity from elbow to shoulder. Segment 7 is passed from the shoulder across the upper back and then from the upper back across the top of the opposite shoulder and then brought vertically down across the front of the chest with its hook and loop fasteners facing the chest from the top of the shoulder where attachment is achieved by fastener 8 to the rear surface 2 of the horizontal segment 3.

The side member 13 of the immobilization segment 5 is brought vertically upward with its fastener 14 facing away from the chest and attached by the fastener 14 to the foam side 1 of the suspensory segment 7 that is facing the chest, thus further securing suspension of the involved upper extremity. The foregoing maneuvers accomplish suspension of the involved upper extremity. The side member 11 of the suspension segment 7 is then wrapped around the arm of the involved upper extremity keeping the hook and loop fastener 12 facing away from the wearer and then mating the fastener 12 to the rear foam surface 2 of the suspension segment 7. This maneuver automatically creates a secure pocket for the elbow of the involved upper extremity as the 60° angled portion 15 of the suspensory segment 7 now becomes opposed to the involved elbow.

The immobilization segment 5. with its hook and loop fastener 6 facing the wearer is then grasped with the hand of the uninvolved upper extremity and passed behind the lower back the wearer then sits back in the chair thus entrapping the immobilization segment 5 between the wearer's back and the back support of the chair preventing retraction of the immobilization segment 5. The immobilization segment 5 is then attached by its fastener 6 to the rear foam surface 2 of the suspensory segment 7 and over the already fastened side member 11 of the suspensory segment 7. This maneuver automatically creates a pocket for the hand of the involved upper extremity as the 60° angled portion 4 of the immobilization segment 5 now engulfs the involved hand. Total immobilization of the involved upper extremity is now complete.

II. For Elevation

After following all the steps for immobilization and total immobilization having been achieved, immobilization segment 5 is unfastened from its point of attachment to the suspensory segment 7 and the side member 11 of the suspensory segment and allowed to retract. The suspensory segment 7 is then unfastened from the horizontal segment 3 and from its attachment to the side member 13 of the immobilization segment 5. The suspensory segment 7 is allowed to retract and then passed between the chest and the involved upper extremity, creating a large rolled-upon-itself configuration of foam behind the arm of the involved upper extremity which acts as a soft buffer support to rest on for the involved upper extremity during elevation in a reclining position. Both suspensory segment 7 and immobilization segment 5 are then extended out to their full length, with the suspensory segment 7 passing along the portion of the foam roll of the forearm that is closest to the chest. The suspensory segment 7 is then attached in its fully extended position by its fastener 8 to the foam of the immobilization segment 5. The end of the immobilization segment 5 (which is also in full extension) is then folded over to attach by its fastener 6 to the foam at the end of the suspensory segment 7.

This maneuver creates a secure loop by which the invention and involved upper extremity may be suspended from an abstract object such as an I.V. pole, thus maintaining constant elevation of the involved upper extremity to decrease swelling. The suspensory segment 7 is further secured to the immobilization segment 5 by wrapping the side member 13 of the immobilization segment 5 around the immobilization segment 5 and the suspensory segment 7 and attaching the side member 13 by its fastener 14 to the foam of the suspensory segment 7.

III. For Suspension

If only suspension of the involved upper extremity is desired so that shoulder exercises can be performed with the invention on supporting the involved upper extremity against gravity, it is necessary to totally remove the immobilization segment 5 from the invention assembly. Therefore, using scissors, a complete transection is made along the imprinted dashed line labeled "cut here" which is appropriate for whichever upper extremity is involved. The scissors transection is performed before the invention is applied to the wearer. After transection is completed the invention is applied exactly the same way as in Section I of the instructions, "FOR IMMOBILIZATION", omitting the portion that pertains to the immobilization segment 5 itself.

I claim:

1. An enhanced sling device adapted to be worn on the torso, upper extremities, and shoulders of a wearer to thereby support, immobilize, and elevate either the right or left injured upper extremity or full shoulder of the wearer, the device comprising:

a panel of flexible material of one piece construction with smoothly contoured perimeter, the panel being flat, with a front surface and a back surface, but flexible enough to contour to the convex and concave surfaces of the upper extremities, shoulders, chest and back of the wearer, the flexible panel having a one piece "T" configuration with a horizontal segment and a vertical segment which is shorter in overall length than the length of the horizontal segment, the horizontal segment and the vertical segment being foldable to envelop the upper extremity on which the device is worn suspended from the shoulders, chest and back of the wearer; and a plurality of individual pieces of hook and loop fastener material placed on the front surface of the panel, substantially adjacent to the ends of each of the horizontal segment and the vertical segment to provide fixation of the panel of flexible material at preselected points, to thereby provide a sling device which is multifunctional and adapted for use on either the right or left extremity;

wherein the vertical segment has two elongated side members disposed parallel to one another, and each vertical segment side member has a rectangular piece of hook and loop fastener material at an inferior end of each side member on the panel front surface disposed between two long edges of the corresponding vertical segment and one inch from an inferior end thereof;

and further wherein the vertical segment has an elongated central member disposed between and parallel to the two side members, and a piece of hook and loop fastener material at an inferior end of the central member on the front surface of the panel.

2. The device according to claim 1 wherein all junction points of all segments of the panel are rounded to decrease stress risers and thereby reduce tearing forces.

3. The device according to claim 1 wherein the horizontal segment has two long edges and two opposed ends and a rectangular piece of hook and loop fastener material on each of the two opposed ends on the front surface of the panel, between the two long edges of the horizontal segment.

4. The device according to claim 3 wherein the horizontal segment is of elongated rectangular configuration.

5. The device according to claim 3 wherein the horizontal and vertical segments of the panel meet at axillary junctions of 60° that begin on a lateral aspect of each side member of the vertical segment and extend from the superior ends of the side members to the inferior long edge of the corresponding horizontal segment.

6. The device according to claim 1 wherein the central member has a width which is twice the width of each side member.

7. The device according to claim 1, wherein the central member of the vertical segment is separated from each of the side members by a distance of ½ the width of the side members, and the side members being of equal width.

8. The device according to claim 1 wherein the flexible material of which the panel is composed is a flexible material which allows hook and loop fastening material to adhere directly to the flexible material and also allows the circulation of air and drainage of adjacent body fluids while still acting as a barrier to the external surroundings.

9. The device of claim 8, wherein the flexible material of which the panel is formed is selected from the group consisting of polyether open cell foam and nylon laminated polyether open cell foam.

10. The device according to claim 1 wherein the panel has a plurality of perforations, non-confluent extending completely through the full thickness of the device opening onto each surface.

11. The device according to claim 1 wherein the vertical segment is of rectangular configuration joined to the horizontal segment in confluent, one piece construction, and a central longitudinal axis of the vertical segment overlaps a central transverse axis of the horizontal segment.

12. The device according to claim 11 wherein the vertical segment of the panel is composed of three members that are of equal length.

13. The device according to claim 1 wherein the horizontal and vertical segments of the panel meet at axillary junctions (4 and 15) of 60°, to thereby form pockets adapted for the elbow and hand of the involved upper extremity when the vertical and horizontal segments of the panel are folded upon each other and the upper extremity and torso of the wearer.

14. The device according to claim 1 wherein the width of the horizontal segment of the panel is equal to ½ the width of the vertical segment of the panel.

15. The device according to claim 1 wherein the a length of the horizontal segment of the panel is equal to $5\frac{1}{3}$ times the length of the vertical segment of the panel in a large size of the enhanced sling device; 6 times the length of the vertical segment in a medium size of the enhanced sling device; and $4\frac{1}{3}$ times the length of the vertical segment in a small size of the enhanced sling device.

16. The device according to claim 1 wherein the vertical segment of the panel is divided into three members of rectangular configuration, disposed lengthwise and parallel to one another.

17. A device for supporting the torso, upper extremities, and shoulders, the device comprising:

a flexible, flat panel of one piece construction with a smoothly contoured perimeter having a "T" shaped configuration comprised of a vertical segment and horizontal segment;

an axillary junction extending diagonally between the horizontal and vertical segments and forming a substantially triangular pocket having a sixty degree angle adapted for an elbow or hand when the vertical and horizontal segments are folded upon each other and properly positioned on the upper extremity and torso of the wearer;

the vertical segment further comprising two side members and central member; and a plurality of hook and loop fasteners connected one inch from an end of the two side members and central member on a front surface of the panel.

18. A method of selectively supporting immobilizing and elevating an injured upper extremity of a person, comprising the steps of:

(a) providing a flexible, flat panel of one piece construction with a smoothly contoured perimeter having a "T" shaped configuration with a vertical segment and horizontal segment, a first arm of the horizontal segment being for immobilization and a second arm of the horizontal segment being for suspension of the injured upper extremity, an axillary junction extending diagonally between the horizontal and vertical segments and forming a substantially triangular pocket having an angle adapted for receiving an elbow or hand when the vertical and horizontal segments are folded upon each other and properly positioned on the upper extremity and torso of the wearer; the vertical segment having a first side member and a second side member, the first side member being on the same side of the panel as the first arm of the horizontal member and the second side member being on the same side of the panel as the second arm of the horizontal member, and a central member disposed between the first side member and the second side member; and a plurality of hook and loop fasteners connected to an end of the two side members and central member on a front surface of the panel;

(b) placing the panel with the hook and loop fasteners facing upwardly;

(c) placing the forearm of the injured upper extremity in the central member of the vertical segment;

(d) wrapping the central member around the forearm until the hook and loop fasteners of the central member meet the flexible material of the horizontal segment, thus creating a roll of material around the forearm with the hook and loop fasteners facing away from the body of the person;

(e) passing the second arm of the horizontal segment upwardly and over the shoulder of the injured upper extremity, thereby creating a pocket and placing the elbow of the injured upper extremity into the pocket to thereby support the elbow;

(f) passing the second arm of the horizontal member of the panel behind the neck of the person and downwardly along the chest of the person on the side opposite the injured upper extremity;

(g) mating the hook and loop fasteners on the end of the second arm of the horizontal segment to the flexible material of the panel on the first side member of the vertical segment, and mating the hook and loop fasteners on the first side member of the vertical segment with the foam of the second arm of the horizontal segment, to thereby support and suspend the elbow of the injured upper extremity;

(h) and further selectively cutting away at least a portion of the first arm of the horizontal segment to thereby only suspend the elbow of the injured upper extremity;

(i) and further selectively passing the first arm of the horizontal segment around the lower back of the person and attaching the hook and loop fasteners of the first arm of the horizontal segment to the flexible material of second side member of the vertical segment, thereby creating a support pocket for the hand of the injured upper extremity and firmly and gently securing the injured upper extremity to the chest of the person; and (j) still further selectively releasing the hook and loop fasteners of the first arm of the horizontal segment from the selective attachment thereof to the second side member and attaching the hook and loop fasteners of the first arm of the horizontal member to the flexible material of the second arm of the horizontal member and attaching the hook and loop fasteners of the second arm of the horizontal member to the flexible material of the first arm of the horizontal member to thereby create a double fastener to flexible material attachment area having a loop shape by which to suspend the upper extremity to a support pole for elevating the injured upper extremity.

* * * * *

UNITED STATES PATENT AND TRADEMARK OFFICE
CERTIFICATE OF CORRECTION

PATENT NO. : 6,030,354
DATED : February 29, 2000
INVENTOR(S) : LAKUSIEWICZ, Ronald J.

It is certified that error appears in the above-identified patent and that said Letters Patent are hereby corrected as shown below:

Column 1, line 12, after "device" delete "hat" and insert --that--.

IN THE CLAIMS:

Claim 15, column 8, line 59, before "length" delete --a--.

Signed and Sealed this

Twenty-fourth Day of April, 2001

*Attest:*

NICHOLAS P. GODICI

*Attesting Officer*     *Acting Director of the United States Patent and Trademark Office*